(12) United States Patent
Deininger et al.

(10) Patent No.: US 11,285,332 B2
(45) Date of Patent: Mar. 29, 2022

(54) MEDICAL DEVICE HOUSINGS DEFINING A LEAD BORE AND DEVICE COMPARTMENT

(71) Applicant: MEDTRONIC, INC., Minneapolis, MN (US)

(72) Inventors: Steven Deininger, Plymouth, MN (US); Randy Roles, Elk River, MN (US); Paul Eichstaedt, Blaine, MN (US)

(73) Assignee: MEDTRONIC, INC., Minneapolis, MN (US)

(*) Notice: Subject to any disclaimer, the term of this patent is extended or adjusted under 35 U.S.C. 154(b) by 73 days.

(21) Appl. No.: 16/537,485

(22) Filed: Aug. 9, 2019

(65) Prior Publication Data

US 2021/0038901 A1 Feb. 11, 2021

(51) Int. Cl.
*A61N 1/05* (2006.01)
*A61N 1/375* (2006.01)

(52) U.S. Cl.
CPC ......... *A61N 1/3754* (2013.01); *A61N 1/0534* (2013.01); *A61N 1/37514* (2017.08)

(58) Field of Classification Search
CPC .............. A61N 1/3754; A61N 1/37514; A61N 1/0534; A61N 1/375; A61N 1/3752; A61N 1/3758; A61N 1/378; A61N 1/3962; A61N 1/37294; A61N 1/3756; A61N 1/3787
See application file for complete search history.

(56) References Cited

U.S. PATENT DOCUMENTS

| | | | |
|---|---|---|---|
| 3,866,616 A | 2/1975 | Purdy et al. | |
| 4,112,953 A | 9/1978 | Shanker et al. | |
| 4,479,489 A | 10/1984 | Tucci | |
| 4,934,366 A | 6/1990 | Truex et al. | |
| 5,456,698 A | 10/1995 | Byland et al. | |
| 5,571,146 A * | 11/1996 | Jones | A61N 1/3752 607/37 |
| 6,498,952 B2 | 12/2002 | Imani et al. | |
| 6,505,073 B2 | 1/2003 | Gramse | |
| 7,110,819 B1 | 9/2006 | O'Hara | |
| 7,630,772 B1 | 12/2009 | Walsh | |
| 9,162,072 B2 | 10/2015 | Singhal et al. | |
| 9,289,615 B2 * | 3/2016 | Spadgenske | H01R 43/16 |
| 9,757,573 B2 | 9/2017 | Glynn et al. | |
| 9,968,792 B2 | 5/2018 | Glynn et al. | |
| 9,968,793 B2 | 5/2018 | Glynn et al. | |

(Continued)

OTHER PUBLICATIONS

PCT/US2020/042868 International Search Report and Written Opinion dated Oct. 2, 2020.

*Primary Examiner* — Carl H Layno
*Assistant Examiner* — Anh-Khoa N Dinh
(74) *Attorney, Agent, or Firm* — Withers & Keys, LLC

(57) ABSTRACT

Medical devices include a housing that defines both a lead bore and a compartment. A separate housing may be inserted into the compartment where the separate housing may include the electrical circuitry of the medical device such as circuitry that provides stimulation and/or sensing. Electrical conductors interconnect terminals of the separate housing to electrical connectors within the lead bore. The two housings may have different shapes and may be constructed of different materials. The housing that defines the lead bore and compartment may be shaped and sized for a specific implantation site while providing the compartment that is shaped and sized for the separate housing.

17 Claims, 9 Drawing Sheets

(56) References Cited

U.S. PATENT DOCUMENTS

| | | | |
|---|---|---|---|
| 2002/0138114 A1* | 9/2002 | Gramse | A61N 1/3758 607/37 |
| 2006/0167534 A1* | 7/2006 | Malinowski | A61N 1/375 607/115 |
| 2007/0254212 A1* | 11/2007 | Viavattine | A61N 1/378 429/164 |
| 2008/0033500 A1 | 2/2008 | Strother | |
| 2015/0051676 A1* | 2/2015 | Van Funderburk | B23K 1/19 607/116 |
| 2015/0066114 A1 | 3/2015 | Bunyan et al. | |
| 2016/0100887 A1 | 4/2016 | Wu et al. | |
| 2016/0121125 A1* | 5/2016 | Kast | A61N 1/3754 607/116 |
| 2018/0015290 A1 | 1/2018 | Deininger | |
| 2018/0243569 A1* | 8/2018 | Malinowski | A61N 1/375 |
| 2018/0272134 A1 | 9/2018 | Tahmasian et al. | |

\* cited by examiner

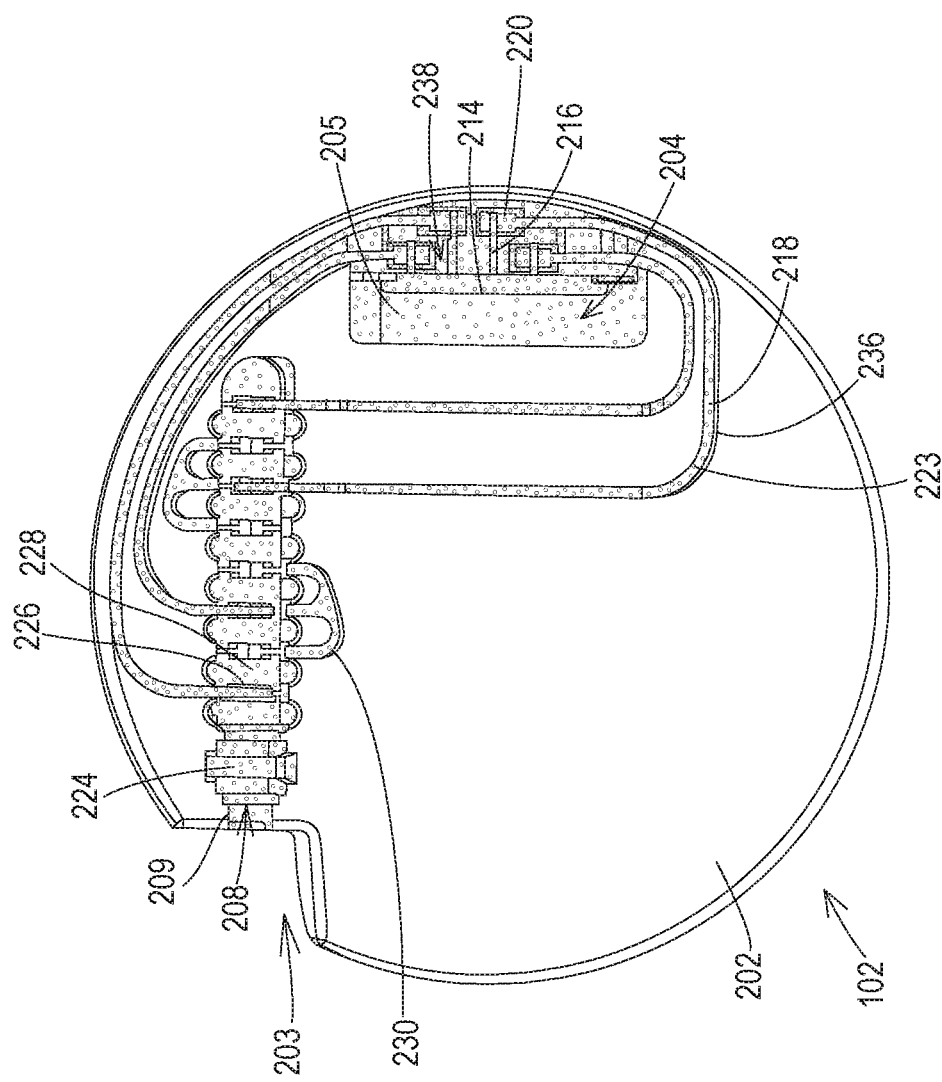

MEDICAL DEVICE HOUSINGS DEFINING A LEAD BORE AND DEVICE COMPARTMENT

TECHNICAL FIELD

The present application relates to medical devices. More particularly, the present application relates to medical devices that define a lead bore and a device compartment.

BACKGROUND

Medical device that provide electrical stimulation and/or physiological sensing require an implantation site within the body of the patient that can accommodate the size and shape of the device while minimizing the intrusiveness experienced by the patient. Typically, a pocket is created within an area of soft tissues of the patient that is nearest the stimulation site while also being a convenient location for purposes of implantation and long-term use, such as below the clavicle for upper body stimulation sites. However, the nearest implantation site within an area of soft tissues may be distant from the stimulation therapy site where the stimulation and/or sensing occurs within the body.

To address this distance and to provide a smaller object at the therapy site, a medical lead is implanted to carry the stimulation and/or sensing signals between the medical device and the therapy site. A distal end of the lead that has electrodes is routed to the therapy site within the body while a proximal end is routed to the medical device to establish electrical connectivity to the medical device. Electrical conductors within the lead body carry the signals.

In some cases, the distance of the route that the lead will follow between the implantation site of the medical device and the therapy site exceeds the length of the medical lead, and in that case a lead extension is also implanted. The lead extension has a proximal end that connects to the medical device to establish electrical connectivity, and the proximal end of the lead is connected to a distal end of the lead extension to further establish electrical connectivity. While the lead extension eliminates the issue of distance in some cases, the lead extension adds to the complexity of the medical system and implantation procedure.

SUMMARY

Embodiments address issues such as these and others by providing a medical device that includes two housings. A first device housing includes the electrical circuitry for providing stimulation and/or sensing functions. A second device housing includes a compartment where the first device housing may be inserted, and the second device housing provides a lead bore where the proximal end of the lead may be inserted. The second device housing may be adapted for one or more locations within the body of the patent that might be unsuitable for the first device housing, such as locations that are more convenient and/or closer to the therapy site than would otherwise be possible.

Embodiments provide an implantable medical device that includes a first device housing and electrical circuitry within the first device housing. The electrical circuitry comprises electrical terminals that are present outside of the first device housing. The implantable medical device further includes a second device housing that has a lead bore and a device housing compartment. The first device housing is present within the device housing compartment, and electrical connectors are present within the lead bore. Electrical conductors electrically connect the electrical terminals to the electrical connectors.

Embodiments provide an implantable medical system that includes an implantable medical device and an implantable medical lead. The implantable medical device includes a first device housing and electrical circuitry within the first device housing. The electrical circuitry includes electrical terminals that are present outside of the first device housing. The implantable medical device includes a second device housing that has a lead bore and a device housing compartment. The first device housing is present within the device housing compartment, and electrical connectors are present within the lead bore. Electrical conductors electrically connect the electrical terminals to the electrical connectors. The implantable medical lead has a proximal and distal end, and the proximal end is present within the lead bore.

Embodiments provide a method of providing stimulation therapy that involves implanting an implantable medical device and implanting an implantable medical lead. The implantable medical device being implanted includes a first device housing and electrical circuitry within the first device housing. The electrical circuitry includes electrical terminals that are present outside of the first device housing. The implantable medical device being implanted further includes a second device housing comprising a lead bore and a device housing compartment, and the first device housing is present within the device housing compartment. Electrical connectors are present within the lead bore, and electrical conductors electrically connect the electrical terminals to the electrical connectors. The implantable medical lead being implanted includes a proximal and a distal end, and the distal end is positioned at a stimulation site while the proximal end is being inserted into the lead bore.

DESCRIPTION OF THE DRAWINGS

FIG. 4A shows a bottom view of an embodiment of the medical device.

DETAILED DESCRIPTION

Embodiments include medical devices that have two housings where a first device housing includes the circuitry for providing stimulation and/or sensing and the second device housing includes a compartment for the first device housing. The second device housing also includes a lead bore that receives a proximal end of a medical lead, and the lead bore includes electrical connectors for establishing electrical connectivity with the proximal end of the lead. Electrical conductors are present within the second device housing and electrically interconnect electrical terminals of the first device housing with the electrical connectors within the lead bore.

Figure 1:
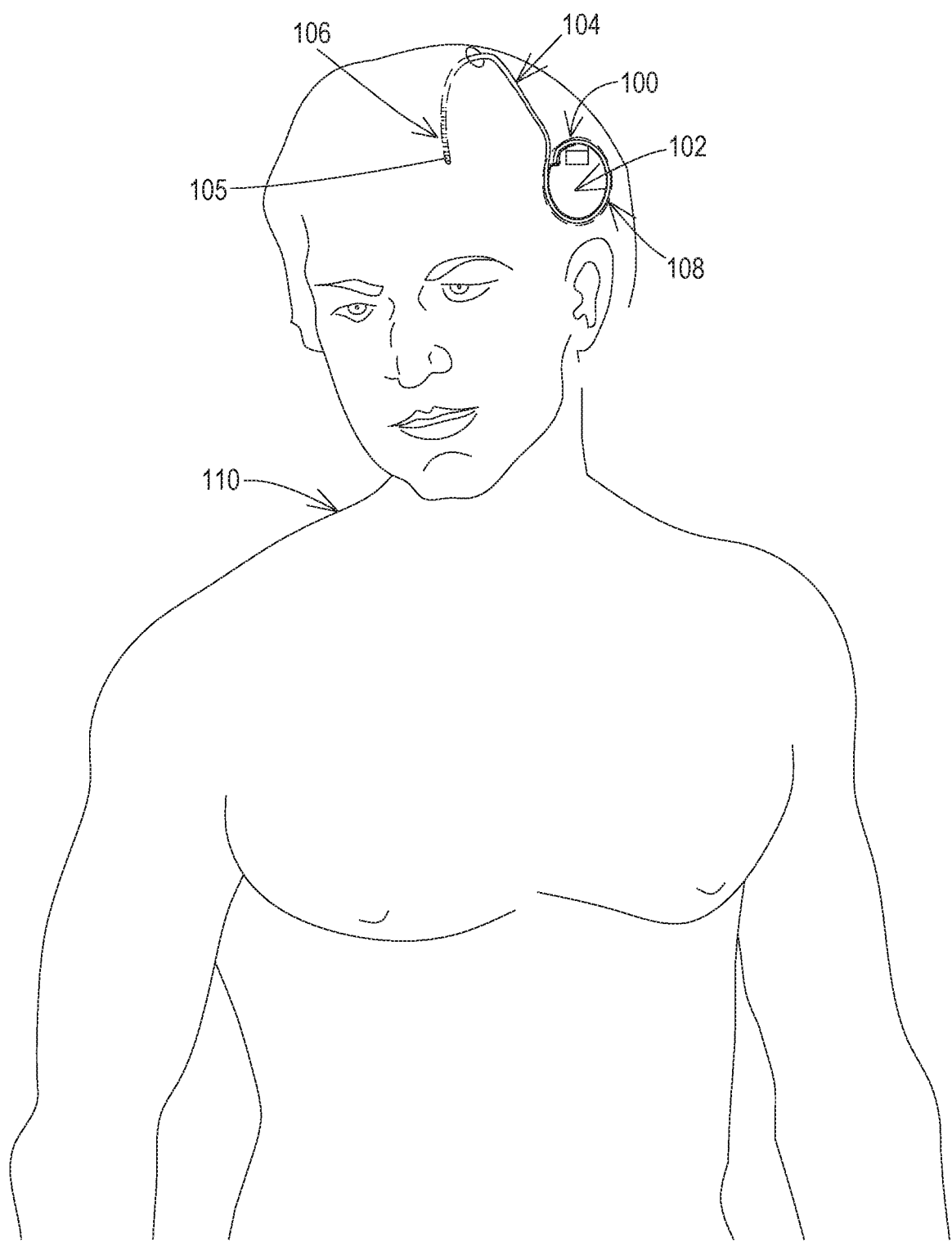
FIG. 1 shows an example of the implantation site for an embodiment of a medical system.

FIG. 1 shows an example of a medical system 100 that has been implanted into a patient 110. In this example, the patient is receiving deep brain stimulation therapy which provides electrical stimulation and/or sensing at a therapy site within the brain. It will be appreciated that embodiments of the medical system 100 may be used for other purposes and in other locations within the body of the patient 110. For instance, the medical system may be used for other forms of neurological stimulation and/or sensing such as spinal cord sensing and/or stimulation, peripheral nerve sensing and/or stimulation, as well as cardiac sensing and/or stimulation, and the like.

The medical system 100 includes a medical device 102 and a medical lead 104 that is coupled to the medical device 102. In this example, the medical device 100 is implanted directly onto the skull of the patient 110. An area 108 may be prepared on the skull to create a depression for the positioning of the medical device 102 subcutaneously in the area 108. This allows the medical device 102 to be positioned much closer to the hole within the skull where the lead 104 is inserted compared to a typical implantation site near the clavicle so that no lead extension is needed in this example.

As shown in FIG. 1, the medical lead 104 extends from the medical device 102 to the insertion hole within the skull. The medical lead 104 extends through the brain to where distal end 106 of the lead 104 having electrodes 105 reaches the therapy site. The medical device 102 being located on the skull may then exchange stimulation and/or sensing signals with the electrodes 105 that have established an electrical interface to the brain tissue. It will be appreciated that the implantation site of the medical device 102 as shown in FIG. 1 is only an example, and that the medical device 102 may be implanted in various other locations on the skull or on other parts of the body of the patient 110.

While this example of FIG. 1 shows a percutaneous lead 104 implanted within the brain of the patient 110, it will be appreciated that the medical system 100 that includes the medical device 102 may be implanted in many other areas of the body of the patient 110 while utilizing aspects of the embodiments disclosed herein. It will also be appreciated that other variations in the medical system 100 may exist, such as utilizing other types of leads including paddle-style leads and the like.

Figure 2:
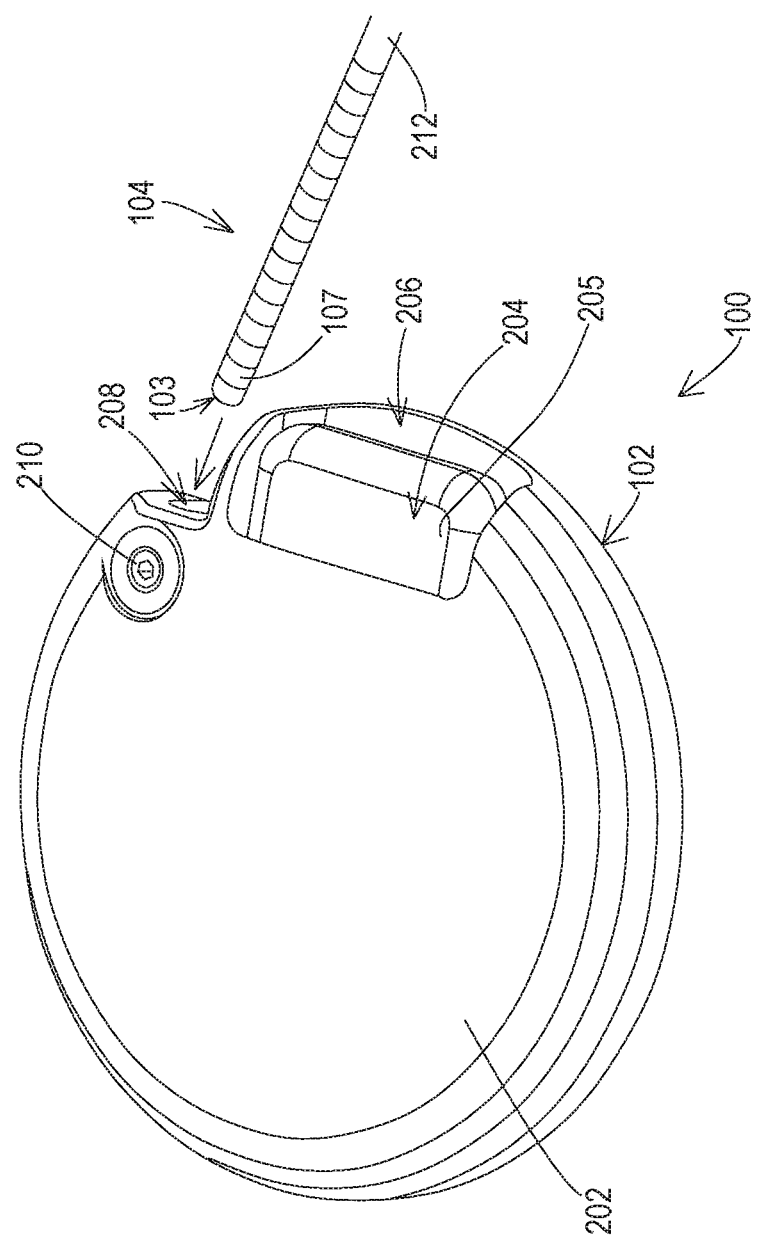
FIG. 2 shows a top view of an example of a medical system where a lead is being inserted into an embodiment of a medical device that includes first and second device housings.
Figure 3:
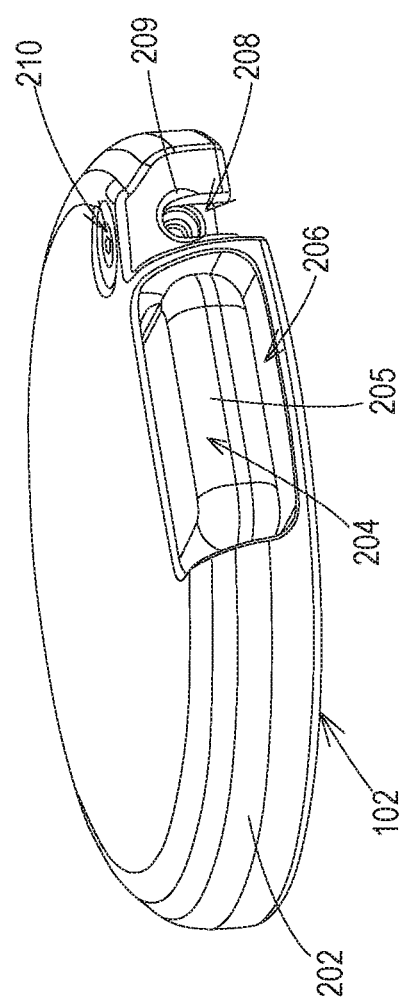
FIG. 3 shows side view of an embodiment of the medical device.

FIGS. 2 and 3 provide a more detailed view of the medical device 102. Here, it can be seen that the medical device 102 includes a first device housing 204 that is positioned within a compartment 206 that is formed by a second device housing 202. As discussed in further detail below, the first device housing 204 encloses electrical circuitry such as a stimulation engine, sensing circuits, a controller, a battery, and the like. Thus, the first device housing 204 may be assembled as a complete unit and then subsequently inserted into the compartment 206 of the second device housing 202 where the medical device 102 may then be completed. A medical adhesive or similar biocompatible material can be applied to fill in any voids that are present between the first device housing 204 and the second device housing 202. The first device housing 204 of this example includes a main housing portion 205 as well as a top cap 214, shown in FIGS. 4A and 6, which are discussed in more detail below. While the first device housing 204 is shown as having a rectangular shape with the top cap 214, it will be appreciated that other shapes and configurations are also possible to allow the first device housing 204 to be inserted into an appropriately shaped and sized compartment 206 of the second device housing 202.

Including both the first device housing 204 and the second device housing 202 for the medical device 102 offers several benefits. The first device housing 204 may be constructed of a shape and size so as to accommodate the desired circuitry, battery and the like regardless of the outer shape of the second device housing 202. The first device housing 204 may also be constructed of a different material than the second device housing 202, such as by utilizing a biocompatible metal or other electrically conductive material that offers better shielding from electromagnetic interference. This allows the first device housing to have a more universal application.

The second device housing 202 may be created with a shape and material that are more specific to the particular location being implanted. For example, the second device housing 202 may be constructed with a round disc-like shape as shown to better fit within a round depression created in the skull. Furthermore, the second device housing 202 may be constructed of a material such as a biocompatible polymer that offers protection for the first device housing 204 while also providing a suitable interface to the bone and subcutaneous tissues at the particular area of implantation.

The second device housing 202 also provides a lead bore 208 where electrical connectors are located, and the lead bore 208 includes an exterior opening 209. As shown in FIG. 2, a proximal end 103 of the medical lead 104 is being inserted through the opening 209 and into the lead bore 208. The proximal end 103 of the lead 104 includes several proximal contacts 107 attached to a lead body 212 that establish electrical connections within the connectors within the lead bore 208. The proximal contacts 107 are electrically connected by internal conductors of the lead 104 with the distal electrodes 105 shown in FIG. 1. Once the proximal end 103 is fully inserted, the lead 103 may be secured in place by a set screw 210 that tightens against the proximal end 103, such as against one of the proximal contacts 107.

While the example shown has the round disc-like shape, it will be appreciated that the second device housing 202 may have many other shapes in other examples while providing both a lead bore 208 and a compartment 206 for the first device housing 204. Furthermore, the orientation of the compartment 206 and lead bore 208 may vary from the parallel configuration shown, such as where the longitudinal dimension of each forms an angle with respect to each other, including a perpendicular orientation. Thus, the round disc-like shape is shown only for purposes of demonstrating one example. Furthermore, while the second device housing of this example may be constructed of a polymer such as polysulfone, or polyether ether ketone (PEEK) and the like, it will be appreciated that other biocompatible materials may instead be used such as a biocompatible metal. However, with a conductive material such as metal, the channels and bays should be coated with a non-conductive material such as polysulfone to electrically isolate the second housing from the conductors and connectors.

While the first housing 204 is located in the compartment 206, it can be seen in the example shown that a portion of the end of the first housing 204 is not covered by the second housing 202. Furthermore, this exposed portion of the first housing 204 may remain uncovered by medical adhesive, so that if the first housing 204 is constructed of a conductive material such as a metal, the first housing 204 may act as a node of the stimulation and sensing circuits, such as for unipolar stimulation. Additionally, for embodiments where the second housing 202 is constructed of a conductive material such as a metal, the second housing 202 may establish electrical contact with a conductive portion of the first housing 204 so that the second housing 202 also forms the electrical node of the stimulation and sensing circuits.

Figure 4B:
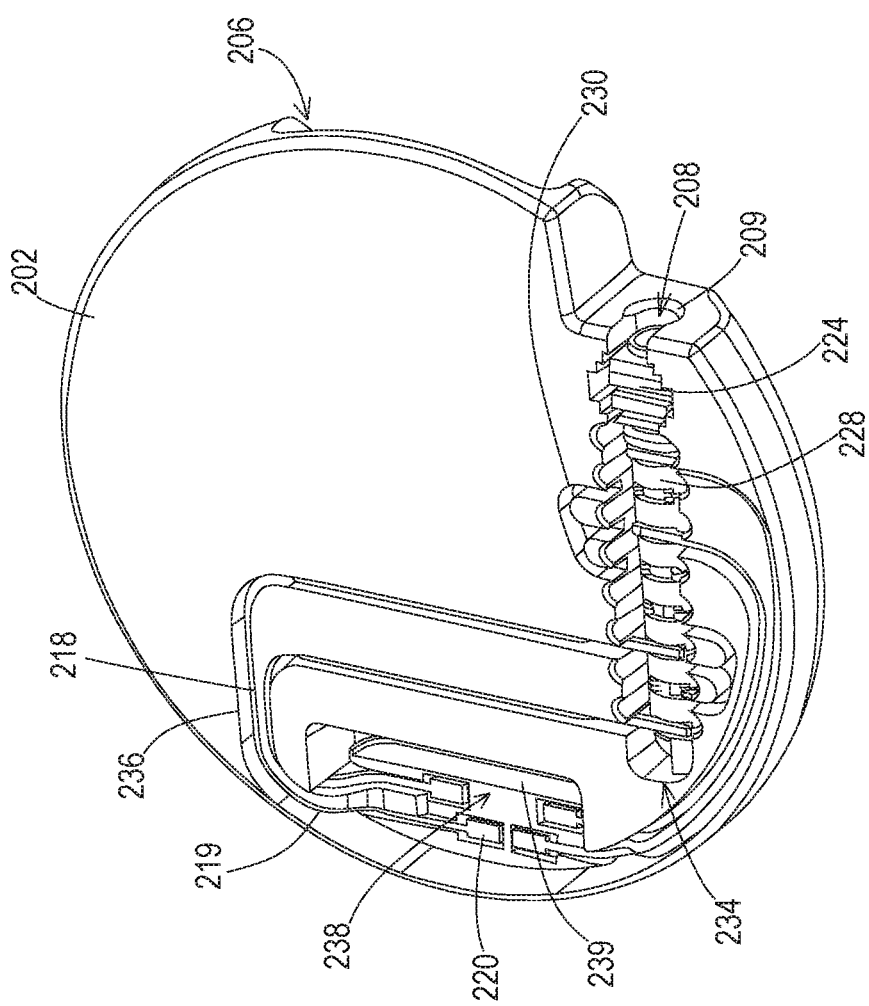
FIG. 4B shows a bottom perspective view of an embodiment of the medical device prior to insertion of the first device housing into the second device housing.
Figure 5:
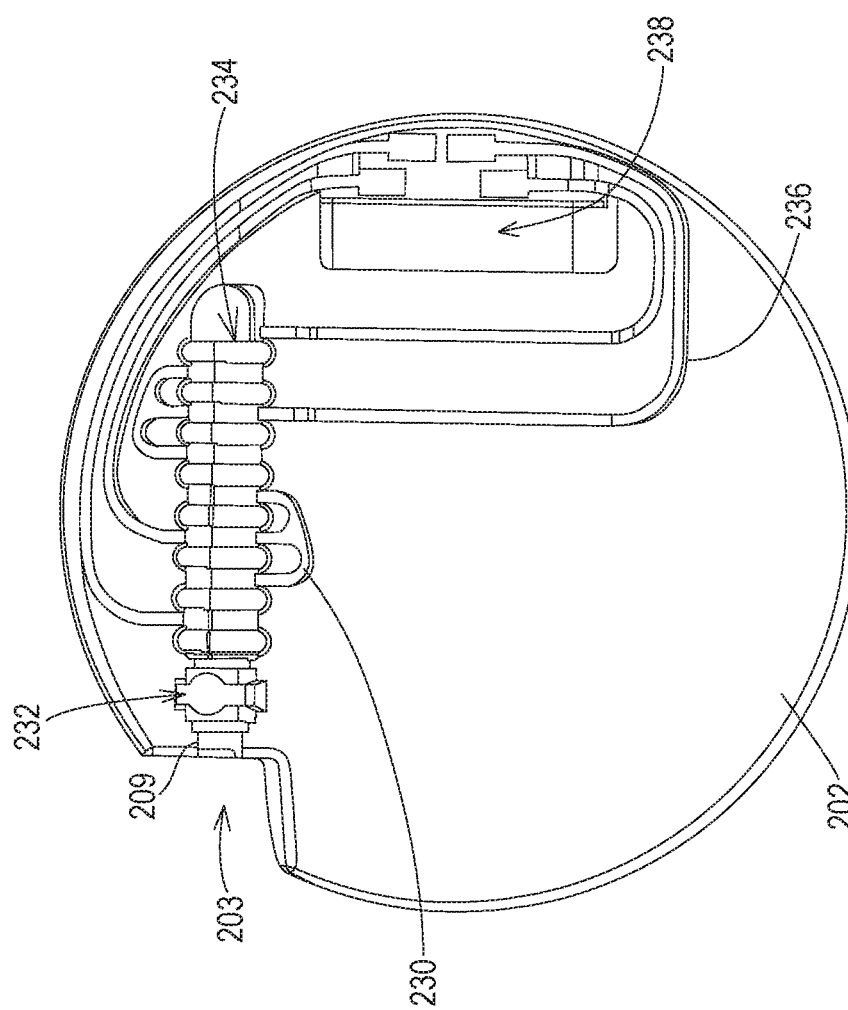
FIG. 5 shows a bottom view of the second device housing.

FIG. 4A shows the underside of this example of a complete medical device 102 while FIG. 4B shows the underside in perspective without the first device housing 204 being inserted. FIG. 5 shows the underside of the second device housing 202 alone. For this medical device 102, the second device housing 202 may be molded or otherwise constructed with features that allow for the inclusion of the first device housing 204 within the compartment 206 and for the electrical connectivity that is necessary between the first device housing 204 and electrical connectors 226 within the lead bore 208 of the second device housing 202.

As shown in FIG. 5, a first bay 234 and a second bay 238 that are open to the exterior are formed in the underside of the second device housing. The second device housing 202 provides channels 236 that extend from the first bay 234 to the second bay 238. The depth of the bays 234, 238 and channels 236 in this example can be seen in the perspective view of FIG. 4B. Also shown in FIG. 5, an aperture 232 is present in the wall of the first bay 234 to provide a location for a set screw block and corresponding set screw 210 of FIG. 2 within the lead bore 208. In this example, the second device housing 202 also forms a notch 203 in the otherwise round periphery of the second device housing 202 where the opening 209 to the lead bore 208 is located. This notch 203 allows the lead 104 to begin an arc as it extends away from the opening 209 so as to then wrap around the second device housing 202 one or more times before extending to the hole in the skull in order to provide strain relief.

Figure 7:
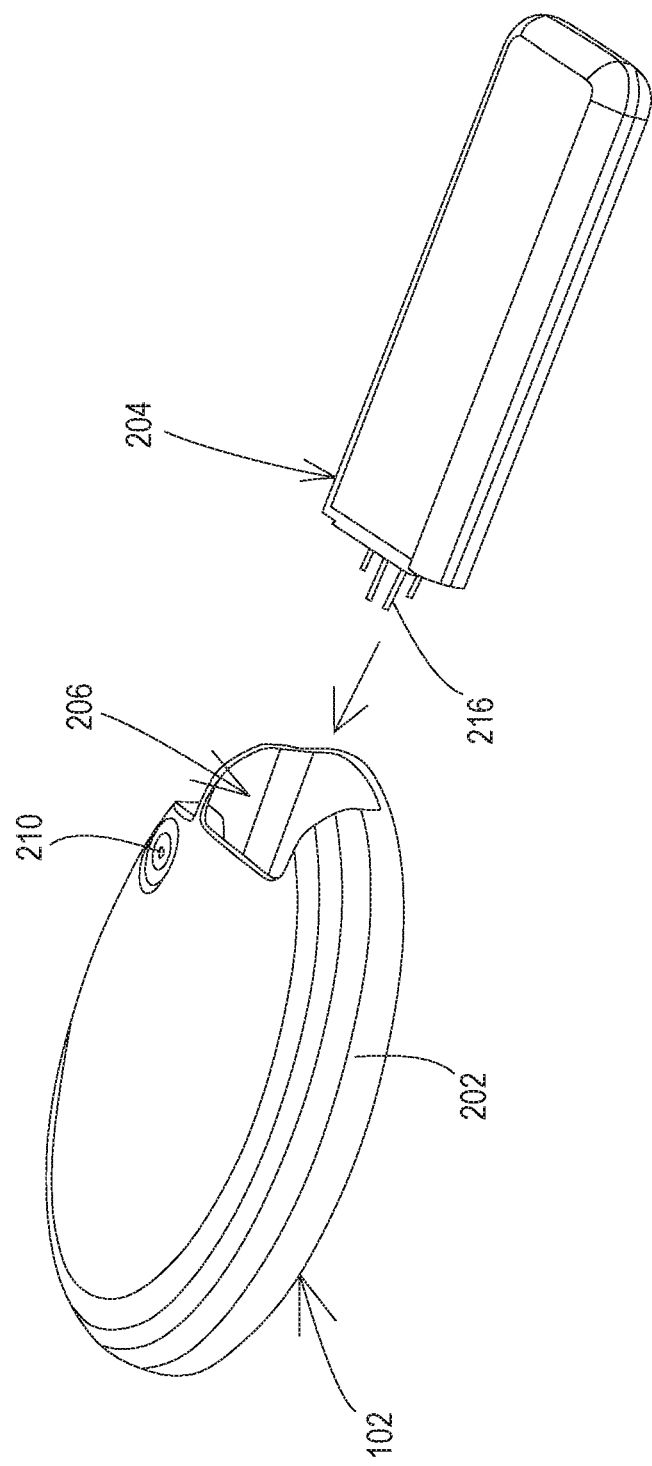
FIG. 7 shows a perspective view of an embodiment of the medical device where the first device housing is being inserted into the second device housing.

As shown in FIGS. 4A and 4B, various items are present within the first bay 234, and hence within the lead bore 208 that is further defined by the first bay 234, including the set screw block 224 and electrical connectors 226 separated by non-conductive seals 228. FIG. 4A shows a top end of the first device housing 204 is positioned within the second bay 238 upon the first device housing 204 being inserted into the compartment 206 as shown in FIG. 7. A wall 239 is shown in the bay 238 in FIG. 4B which provides a hard stop for the insertion of the first device housing, as the top cap 214 abuts the wall 239 once the first device housing 204 is fully inserted.

Electrical terminals 216 in the form of feedthrough pins extend from the top cap 214 of the first device housing 204 to corresponding channels 238 once the top cap 214 reaches the wall 239. Electrical conductors 218 are present within the channels 236 where one end of the conductors 218 makes electrical connection to a corresponding electrical connector 226 while another end of the conductors 218 makes electrical connection to a corresponding electrical terminal 216. As can be seen in FIG. 4B, in this example, the conductors 218 include a portion 219 that drops to a lower position within the bay 238 so that the pad 220 resides immediately beneath the terminals 216 once the first device housing 204 is inserted. To facilitate creating contact, such as a weld or other electrically conductive bond between the conductor 218 and the terminal 216, the end of the conductor 218 may form a conductive pad 220 with increased surface area. Alternatively, other forms of contact may occur between the conductor 218 and terminal 216, such as a frictional engagement via a spring loaded connector of the conductor 218 in place of the conductive pad 220 that frictionally contacts the terminal 216.

Figure 6:
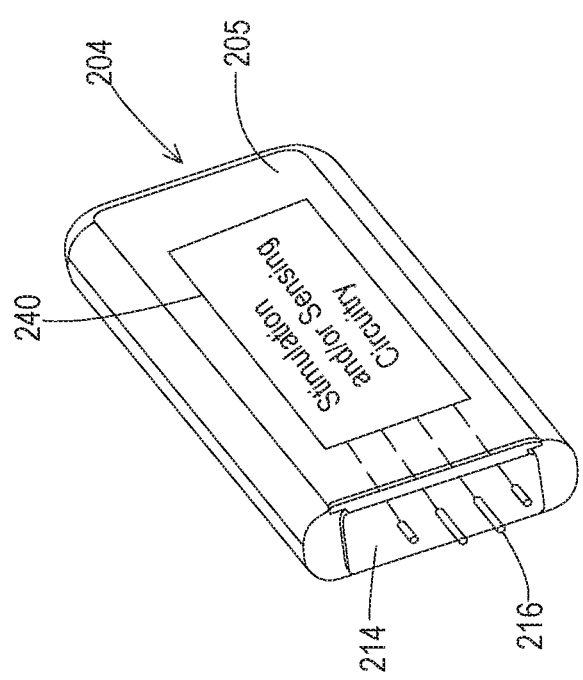
FIG. 6 shows a perspective view of the first device housing.

The top end of the first device housing 204 in relation to stimulation and/or sensing circuitry 240 is shown in more detail in FIG. 6. As can be seen, the main portion 205 of the first device housing encloses the circuitry 240 while the top cap 214 provides for the electrical terminals 216 to be exposed outside of the first device housing 204 for purposes of electrical connection to the conductors 218. The top cap 214 may establish a feedthrough that is a hermetic seal to further protect the circuitry 240 from bodily fluids that surround the medical device 102. Additionally, the top cap 214 may provide a filtered feedthrough to reduce the amount of electrical noise that may be present on the conductors 218 that reaches the circuitry 240.

Once the electrical connections have been established among the various components, a medical adhesive or other similar filler material 223 (represented as dots in FIG. 4A merely for purposes of illustration) may be applied to the underside of the second device housing 202. The filler material 223 fills both the first bay 234 and the second bay 238 to encapsulate the components installed within those bays 234, 238. Additionally, the filter material 223 is applied within the channels 236 to encapsulate the conductors 218. The filler material 223 may be applied to completely fill the bays 234, 238 and channel 236 and create a flush underside surface for the second device housing 202. The filler 223 thereby electrically isolates the components within the bays 234, 238 and channels 236.

Rather than installing all of the components and electrical connections prior to applying the filler material 223, other approaches may be used. For instance, the components may be installed in the bay 234 and the channels 236 and then the bay 234 and channels 236 are filled while the bay 238 remains unfilled. Subsequently, the first device housing 204 is inserted into the compartment 206 with bonds being created between the terminals 216 and the pads 220, and then the second may 238 is filled. As another possibility, the order may be reversed where the first device housing 204 is inserted with terminals being bonded to the pads 220 and the bay 238 filled while the bay 234 remains unfilled. Subsequently, the components of the first bay 234 are installed with connectors 226 being bonded to the conductors 218, and the bay 238 is then filled.

Another feature that may be present for some embodiments is also shown in FIGS. 4A, 4B, and 5. A bridging channel 230 may be provided in the second device housing 202 for purposes of containing a bridging conductor that bridges multiple electrical connectors 226 in parallel to the same conductor 218 and hence to the same terminal 216 of the first device housing 204. This may be used where the first device housing 204 has fewer electrical terminals 216 than the lead 204 has proximal contacts 107 and distal electrodes 106. This allows all proximal contacts 107 and distal electrodes 106 to be active electrical nodes of the circuitry 240 when desired. The filler material 223 is also applied to the bridging channels 230 to encapsulate the bridging conductors.

Figure 8:
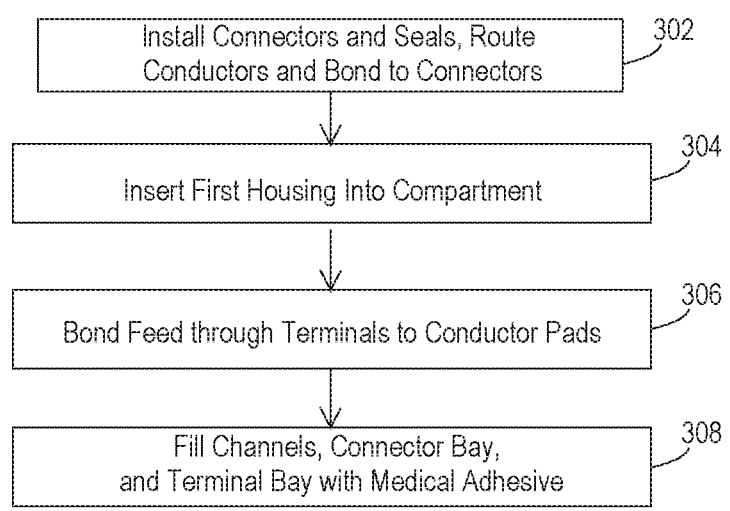
FIG. 8 shows a set of manufacturing operations to create an embodiment of the medical device.

FIG. 8 shows an example of the manufacturing operations that may be performed to create the medical device 102. Initially, at an operation 302, the connectors 226 and seals 228 as well as the set screw block 224 may be installed in the first bay 234. Additionally, the conductors 218 routed through the channels 236 and are bonded to the corresponding connectors 226 such as by a weld. As discussed above, in one example, filler material may be added at this point except for the second bay 238. However, in this example of FIG. 8, all filler material is added at a later point.

At an operation 304, the first device housing is inserted into the compartment 206 of the second device housing 202. As discussed above in relation to FIG. 4B of this example, the second bay 238 includes the wall 239 that acts as a stop for the insertion of the first device housing 204 into the compartment 206, and upon the top cap 214 reaching the wall 239, the terminals 216 are aligned with the pads 220. At an operation 306, the terminals 216 are placed in contact with the conductors, such as by being bonded to the pads 220 via welds or other conductive bonds or by other forms of contact such as a frictional engagement. Once all the electrical connections are established, the bays 234, 238 and channels 236 that have not previously been filled may be filled with the medical adhesive or other biocompatible filler material at an operation 308. The medical device 102 is then ready for implantation.

While embodiments have been particularly shown and described, it will be understood by those skilled in the art that various other changes in the form and details may be made therein without departing from the spirit and scope of the invention.

What is claimed is:

1. An implantable medical device, comprising:
   a first device housing;
   electrical circuitry within the first device housing, wherein the electrical circuitry comprises electrical terminals that are present outside of the first device housing;
   a second device housing comprising a lead bore and a device housing compartment, the first device housing being present within the device housing compartment;
   electrical connectors within the lead bore; and
   electrical conductors electrically connecting the electrical terminals to the electrical connectors, wherein the second device housing comprises channels, wherein the electrical conductors are present within the channels, and further comprising a filler material within the channels and isolating the electrical conductors.

2. The implantable medical device of claim 1, wherein the electrical conductors each include an end comprising a conductive pad.

3. The implantable medical device of claim 2, wherein the electrical terminals each comprise a pin that is in contact with a corresponding one of the conductive pads.

4. The implantable medical device of claim 1, wherein the first device housing comprises metal and wherein the second device housing comprises a polymer.

5. The implantable medical device of claim 1, further comprising a set screw block within the lead bore.

6. An implantable medical device, comprising:
   a first device housing;
   electrical circuitry within the first device housing, wherein the electrical circuitry comprises electrical terminals that are present outside of the first device housing;
   a second device housing comprising a lead bore and a device housing compartment, the first device housing being present within the device housing compartment;
   electrical connectors within the lead bore; and
   electrical conductors electrically connecting the electrical terminals to the electrical connectors, wherein the second device housing comprises a bay, wherein an end of the first device housing and the electrical terminals are present within the bay, and further comprising a filler material within the bay and isolating the electrical terminals and the end of the first device housing.

7. An implantable medical system, comprising:
   an implantable medical device comprising:
      a first device housing;
      electrical circuitry within the first device housing, wherein the electrical circuitry comprises electrical terminals that are present outside of the first device housing;
      a second device housing comprising a lead bore and a device housing compartment, the first device housing being present within the device housing compartment;
      electrical connectors within the lead bore;
      electrical conductors electrically connecting the electrical terminals to the electrical connectors; and
   an implantable medical lead having a proximal and distal end, the proximal end being present within the lead bore, wherein the second device housing comprises channels, wherein the electrical conductors are present within the channels, and further comprising a filler material within the channels and isolating the electrical conductors.

8. The implantable medical system of claim 7, wherein the electrical conductors each include an end comprising a conductive pad.

9. The implantable medical system of claim 8, wherein the electrical terminals each comprise a pin that is in contact with a corresponding one of the conductive pads.

10. The implantable medical system of claim 7, wherein the first device housing comprises metal and wherein the second device housing comprises a polymer.

11. The implantable medical system of claim 7, further comprising a set screw block within the lead bore.

12. An implantable medical system, comprising:
   an implantable medical device comprising:
      a first device housing;
      electrical circuitry within the first device housing, wherein the electrical circuitry comprises electrical terminals that are present outside of the first device housing;
      a second device housing comprising a lead bore and a device housing compartment, the first device housing being present within the device housing compartment;
      electrical connectors within the lead bore;
      electrical conductors electrically connecting the electrical terminals to the electrical connectors; and
   an implantable medical lead having a proximal and distal end, the proximal end being present within the lead bore, wherein the second device housing comprises a bay, wherein an end of the first device housing and the electrical terminals are present within the bay, and further comprising a filler material within the bay and isolating the electrical terminals and the end of the first device housing.

13. A method of providing stimulation therapy, comprising:
   implanting an implantable medical device that comprises:
      a first device housing;
      electrical circuitry within the first device housing, wherein the electrical circuitry comprises electrical terminals that are present outside of the first device housing;

a second device housing comprising a lead bore and a device housing compartment, the first device housing being present within the device housing compartment;
electrical connectors within the lead bore; and
electrical conductors electrically connecting the electrical terminals to the electrical connectors; and
implanting a medical lead having a proximal and a distal end, the distal end being positioned at a stimulation site and the proximal end being inserted into the lead bore, wherein the second device housing comprises channels, wherein the electrical conductors are present within the channels, and further comprising a filler material within the channels and isolating the electrical conductors.

14. The method of claim 13, wherein the electrical conductors each include an end comprising a conductive pad.

15. The method of claim 14, wherein the electrical terminals each comprise a pin that is in contact with a corresponding one of the conductive pads.

16. The method of claim 13, wherein the first device housing comprises metal and wherein the second device housing comprises a polymer.

17. A method of providing stimulation therapy, comprising:
implanting an implantable medical device that comprises:
a first device housing;
electrical circuitry within the first device housing, wherein the electrical circuitry comprises electrical terminals that are present outside of the first device housing;
a second device housing comprising a lead bore and a device housing compartment, the first device housing being present within the device housing compartment;
electrical connectors within the lead bore; and
electrical conductors electrically connecting the electrical terminals to the electrical connectors; and
implanting a medical lead having a proximal and a distal end, the distal end being positioned at a stimulation site and the proximal end being inserted into the lead bore, wherein the second device housing comprises a bay, wherein an end of the first device housing and the electrical terminals are present within the housing, and further comprising a filler material within the bay and isolating the electrical terminals and the end of the first device housing.

* * * * *